United States Patent
Isoda et al.

(10) Patent No.: US 9,874,558 B2
(45) Date of Patent: Jan. 23, 2018

(54) IMMUNOASSAY METHOD LESS AFFECTED BY IMPURITIES

(71) Applicant: Konica Minolta, Inc., Chiyoda-ku, Tokyo (JP)

(72) Inventors: Takeshi Isoda, Sayama (JP); Tomonori Kaneko, Hachioji (JP)

(73) Assignee: KONICA MINOLT, INC., Chiyoda-Ku, Tokyo (JP)

( * ) Notice: Subject to any disclaimer, the term of this patent is extended or adjusted under 35 U.S.C. 154(b) by 0 days.

(21) Appl. No.: 14/655,998

(22) PCT Filed: Nov. 15, 2013

(86) PCT No.: PCT/JP2013/080928
§ 371 (c)(1),
(2) Date: Jun. 26, 2015

(87) PCT Pub. No.: WO2014/103553
PCT Pub. Date: Jul. 3, 2014

(65) Prior Publication Data
US 2015/0355176 A1 Dec. 10, 2015

(30) Foreign Application Priority Data

Dec. 28, 2012 (JP) ................................. 2012-288156

(51) Int. Cl.
*G01N 33/543* (2006.01)
*G01N 33/574* (2006.01)
*G01N 21/64* (2006.01)
*G01N 33/50* (2006.01)

(52) U.S. Cl.
CPC ..... *G01N 33/54393* (2013.01); *G01N 21/648* (2013.01); *G01N 33/50* (2013.01); *G01N 33/57484* (2013.01); *G01N 2021/6439* (2013.01); *G01N 2333/42* (2013.01); *G01N 2333/4724* (2013.01); *G01N 2333/96433* (2013.01); *G01N 2400/00* (2013.01); *G01N 2400/02* (2013.01)

(58) Field of Classification Search
None
See application file for complete search history.

(56) References Cited

U.S. PATENT DOCUMENTS

| | | | |
|---|---|---|---|
| 2009/0061455 A1 | 3/2009 | Sankaran et al. | |
| 2011/0294141 A1* | 12/2011 | Yamashita | G01N 33/57434 435/7.4 |
| 2012/0065089 A1 | 3/2012 | Kuno et al. | |
| 2014/0170772 A1* | 6/2014 | Ide | G01N 21/648 436/501 |

FOREIGN PATENT DOCUMENTS

| | | |
|---|---|---|
| JP | 2002365298 A | 12/2002 |
| JP | 2009053195 A | 3/2009 |
| JP | 2010060293 A | 3/2010 |
| JP | 2010112748 A | 5/2010 |
| JP | 2011169609 A | 9/2011 |
| WO | WO 2010/134592 A1 * 11/2010 | ............. G01N 21/64 |

OTHER PUBLICATIONS

Hornbeck et al. (Current Protocols in Mol. Biol. Enzyme-Linked Immunosorbent Assays (ELISA) 2000, 11.2.1-11.2.22).*
International Search Report corresponding to Application No. PCT/JP2013/080928; dated Feb. 18, 2014, with English translation.
Written Opinion of the International Searching Authority corresponding to Application No. PCT/JP2013/080928; dated Feb. 18, 2014, with English translation.
Extended European Search Report for corresponding EP Application No. 13868754.6 dated Jul. 7, 2016.
K.Fukushima et al: "1,2-Fucosylated and -N-acetylgalactosaminylated prostate-specific antigen as an efficient marker of prostatic cancer", Glycobiology, vol. 20, No. 4, Apr. 1, 2010, pp. 452-460.
Porter et al: "An evaluation of lectin-mediated magnetic bead cell sorting for the targeted separation of enteric bacteria", Jounal of Applied Microbiology., vol. 84, No. C5, Jun. 1, 1998, p. 722-732.
Notification of Reason for Refusal corresponding to Japanese Application No. 2014-554230; dated Jun. 6, 2017.

* cited by examiner

*Primary Examiner* — Peter J Reddig
(74) *Attorney, Agent, or Firm* — Cantor Colburn LLP

(57) ABSTRACT

An object of the present invention is to provide a method of measuring the amount of a compound containing a sugar chain in a biological sample by a sandwich immunoassay method using a labeled lectin, which method is suitable for reduction of noise originating from impurities and determination of the exact amount of a target compound. The present invention provides a method of measuring the amount of a target compound containing a sugar chain in a biological sample by a sandwich immunoassay method using a labeled lectin (including cases where a target compound-capturing substance other than an antibody is used as a ligand), the method containing adding a sugar chain compound which competes (crosses) with impurities contained in the biological sample in binding with the labeled lectin.

17 Claims, 3 Drawing Sheets

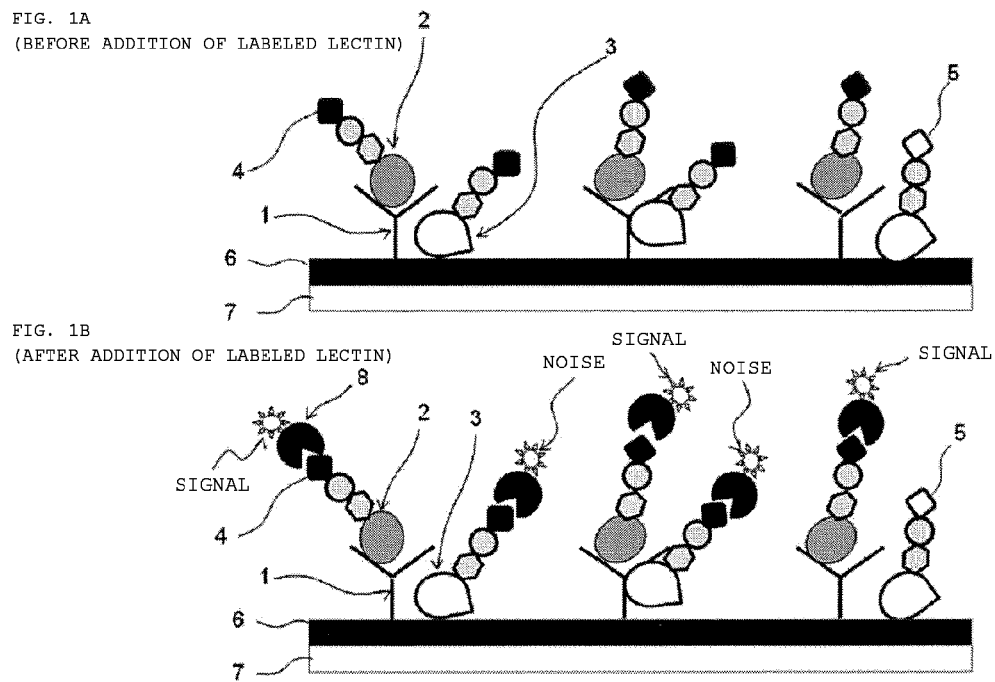

FIG. 2A
(BEFORE ADDITION OF
SUGAR CHAIN COMPOUND)
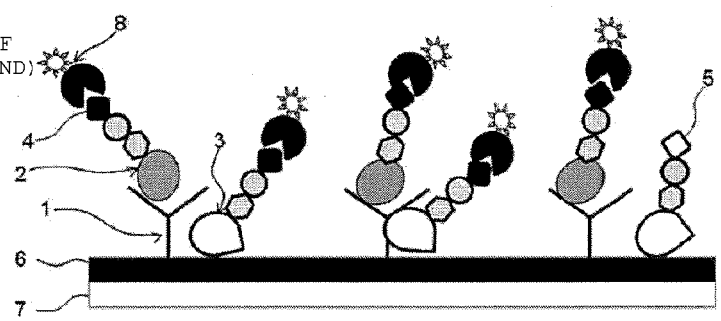
FIG. 2B
(AFTER ADDITION OF
SUGAR CHAIN COMPOUND)
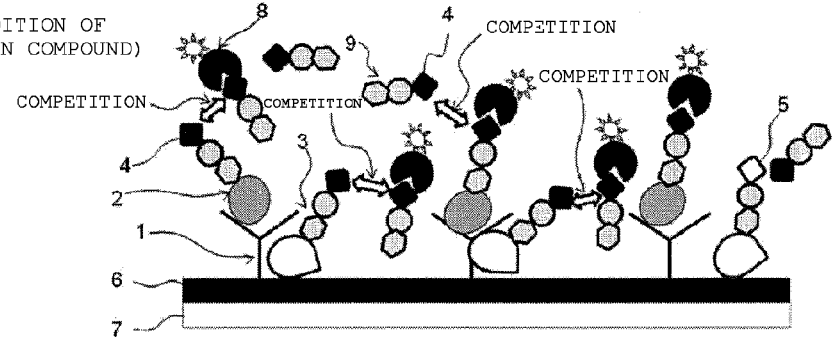
FIG. 2C (AFTER WASHING)
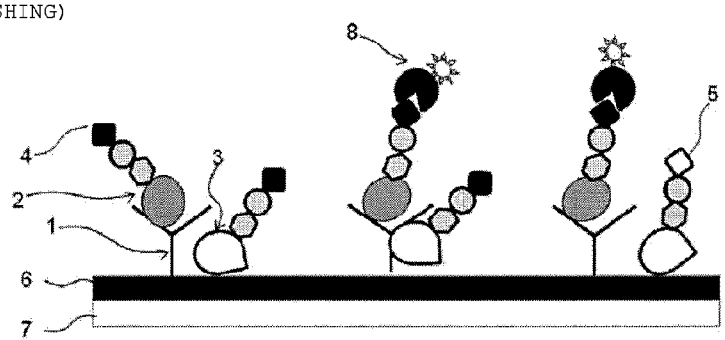

(EXAMPLE OF SOLID-PHASE LAYER IN SPFS)

IMMUNOASSAY METHOD LESS AFFECTED BY IMPURITIES

CROSS REFERENCE TO RELATED APPLICATIONS

This is the U.S. national stage of application No. PCT/JP2013/080928, filed on Nov. 15, 2013. Priority under 35 U.S.C. § 119(a) and 35 U.S.C. § 365(b) is claimed from Japanese Application No. 2012-288156, filed Dec. 28, 2012, the disclosure of which is also incorporated herein by reference.

TECHNICAL FIELD

The present invention relates to a method of measuring the amount of a compound comprising a sugar chain in a biological sample by a sandwich immunoassay method using a labeled lectin. More particularly, the present invention relates to a method of measuring the amount of a compound comprising a sugar chain in a biological sample by a sandwich immunoassay method using a labeled lectin, in which method noise originating from impurities is reduced.

BACKGROUND ART

Today, detection and quantification of a tumor marker, a specific protein or other antigen contained in blood or urine or in other biological sample of human or animal are widely performed for diagnosis in the medical field as well as for research in the fields of biology and biochemistry. As a method of specifically detecting a trace amount of a compound to be measured (antigen), immunoassay is employed. One example thereof is a sandwich method in which an antigen captured by a primary antibody is labeled with a secondary antibody, and a fluorescent antibody method which uses a fluorescent label as a secondary antibody and radioimmunoas say which uses labeling with a radioactive substance have been widely employed.

Meanwhile, lectins are known as proteins binding to a sugar chain that are not produced by an immunological method. Lectins usually have two or more sugar-binding sites per molecule. Generally, proteins and the like that are contained in a biological sample comprise a sugar chain, and there has also been proposed a method in which a lectin that specifically recognizes a sugar chain of an antigen to be measured in place of a secondary antibody in an immunoassay method.

However, in biological samples such as blood (serum and plasma), in addition to an antigen to be measured, a variety of proteins, lipids and other impurities are contained. In immunoassay, due to non-specific adsorption of these impurities to, for example, a primary or secondary antibody or a solid-phase layer (solid-phase support) by which a primary antibody is immobilized to a support (such as a well) and binding of a fluorescent label to the impurities, non-specific signals originating from the impurities are generated to cause background noise.

As an immunoassay method in which non-specific reactions are suppressed, the use of a sugar chain compound having a non-specific reaction-reducing effect has been examined in an immunoassay method using a measurement reagent having a sugar chain (Patent Document 1). In this case, it is believed that the sugar chain compound acts to reduce noise by allowing the added other sugar chain compound to block a reaction site of the measurement reagent having a sugar chain.

In this manner, there have already been made proposals pertaining to noise reduction in the measurement of an antigen in a biological sample by immunoassay; however, from the standpoints of the measurement sensitivity, measurement accuracy, operability, cost and the like, it is critical to select the most effective method in accordance with each biological sample and antigen to be measured, and there is a demand for a proposal pertaining to further noise reduction.

PRIOR ART REFERENCE

Patent Document

[Patent Document 1] JP-A-2010-60293

SUMMARY OF THE INVENTION

Problems to be Solved by the Invention

An object of the present invention is to provide a method of measuring the amount of a compound comprising a sugar chain in a biological sample by a sandwich immunoassay method using a labeled lectin, which method is suitable for reduction of noise originating from impurities and determination of the exact amount of a target compound.

Technical Solution

In an immunoassay by a sandwich method using a labeled lectin, impurities having a sugar chain that exist in a biological sample, such as glycoproteins and glycolipids other than a target compound, also non-specifically bind to a ligand (primary antibody of a sandwich method) for capturing the target compound or a solid-phase layer (solid-phase support) used for immobilization of the ligand onto a support (such as a well) (hereinafter, referred to as "ligand and the like"). In addition, since a lectin used for detection has a certain range in its sugar chain recognizability, a labeled lectin also binds to sugar chains of impurities non-specifically bound to the ligand and the like, and this causes noise generation (see FIG. 1).

The present inventors conducted studies with a focus on the range of sugar chain recognizability and the binding strength of lectins. That is, the present inventors discovered that, by adding a sugar chain compound that competes (crosses) with sugar chains of impurities in a biological sample for binding with a labeled lectin, the sugar chains of impurities bound with the labeled lectin are dissociated at a certain ratio and the thus dissociated labeled lectin and the added sugar chain compound bind with each other, as a result of which the labeled lectin binding to the impurities non-specifically bound to a ligand and the like can be released, thereby completing the present invention (see FIG. 2). In this case, it is preferred that the competition between the sugar chain of the target compound bound with the labeled lectin and the added sugar chain compound be kept in a certain range and the intensity of the signal originating from the target compound be thereby maintained. Thus, the present inventors discovered that it is preferred to keep the dissociation constant between the added sugar chain compound and labeled lectin in a certain range, thereby completing the present invention.

That is, in one aspect of the present invention, the measurement method according to the present invention is as follows:

A method of measuring the amount of a target compound comprising a sugar chain in a biological sample by a sandwich immunoassay method using a labeled lectin (including cases where a target compound-capturing substance other than an antibody is used as a ligand), the method comprising adding a sugar chain compound which competes (crosses) with impurities contained in the biological sample in binding with the labeled lectin.

Advantageous Effects of Invention

According to the present invention, a method of measuring the amount of a compound comprising a sugar chain in a biological sample by a sandwich immunoassay method using a labeled lectin, which method is suitable for reduction of noise originating from impurities and determination of the exact amount of a protein, can be provided.

BRIEF DESCRIPTION OF DRAWINGS

FIG. 1 is a conceptual diagram showing the outline of the generation of noise originating from impurities contained in a biological sample in a conventional sandwich method. The sugar chains of impurities non-specifically bound to a ligand, a solid-phase layer and the like bind with a labeled lectin and this causes noise generation.

FIG. 1A is a conceptual diagram showing the outline of the state of before addition of labeled lectin in a conventional sandwich method. The sugar chains of impurities non-specifically bind to a ligand, a solid-phase layer and the like.

FIG. 1B is a conceptual diagram showing the outline of the state of after addition of labeled lectin in a conventional sandwich method. The sugar chains of impurities non-specifically bound to a ligand, a solid-phase layer and the like bind with a labeled lectin and this causes noise generation.

FIG. 2 is a conceptual diagram showing the outline of the competition (crossing) in binding with a labeled lectin between a sugar chain compound added in the present invention and the sugar chains of impurities contained in a biological sample. By adding the sugar chain compound, the sugar chains of impurities bound with the labeled lectin are dissociated at a certain ratio and the thus dissociated labeled lectin and the added sugar chain compound bind with each other. Consequently, the labeled lectin binding to the impurities that are non-specifically bound to a ligand, a solid-phase layer and the like can be released.

FIG. 2A is a conceptual diagram showing the outline of the state of before addition of sugar chain compound in a conventional sandwich method. Labeled lectin binds not only sugar chains of a target compound but also sugar chains of impurities.

FIG. 2B is a conceptual diagram showing the outline of the state of after addition of sugar chain compound in a conventional sandwich method. By adding the sugar chain compound, the sugar chains of impurities bound with the labeled lectin are dissociated at a certain ration and the thus dissociated labeled lectin and the added sugar chain compound bind each other. Consequently, the labeled lectin binding to the impurities that are non-specifically bound to a ligand, a solid-phase layer and the like can be released.

FIG. 2C is a conceptual diagram showing the outline of the state of after washing in a conventional sandwich method. By removing the labeled lectin released from the solid phase and bound with the sugar chain compound by washing and the like, the noise originating from the impurities in a sandwich method is reduced.

MODE FOR CARRYING OUT THE INVENTION

Figure 3:
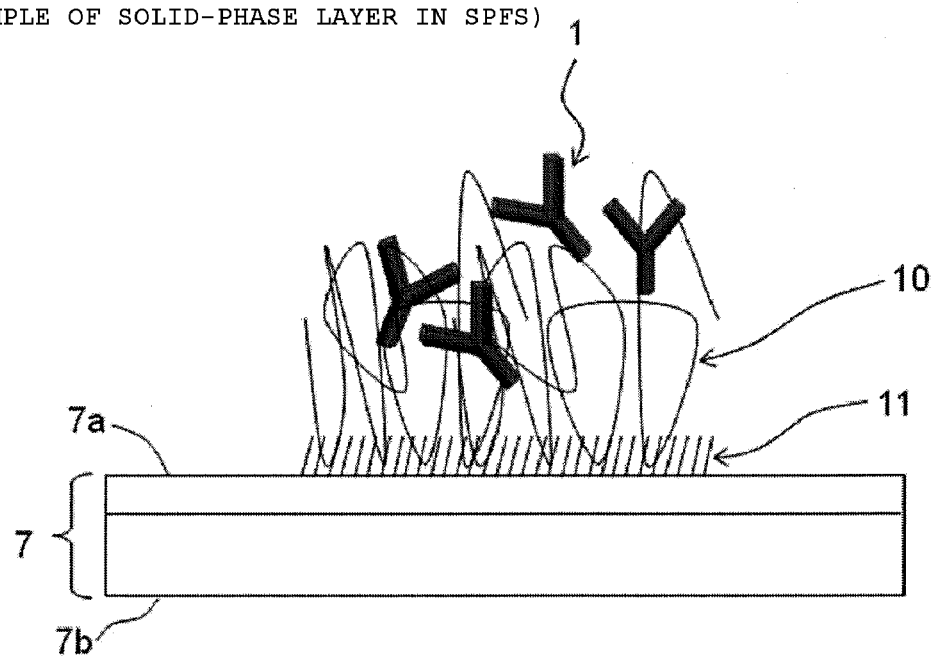
FIG. 3 is a conceptual diagram showing, as an example of a case where SPFS is employed, the outline of a process where a SAM and a solid-phase layer are formed on the support surface and a ligand is immobilized on the solid-phase layer.

The measurement method of the present invention will now be described.
1. Target Compound
(1) Biological Sample The present invention is a method of measuring the amount of a target compound comprising a sugar chain in a biological sample. The biological sample to be measured is not particularly restricted, and examples thereof include blood, serum, plasma, urine, spinal fluid, saliva, cells, tissues, organs and preparations thereof (such as biopsy specimens). Particularly, blood, serum and plasma that potentially contain a tumor antigen and a tumor marker are preferred as the biological sample to be measured.

As required, liquid samples such as blood, serum, plasma, urine, spinal fluid and saliva may be diluted with an appropriate buffer prior to use. Solid samples such as cells, tissues and organs can be homogenized with an addition of an appropriate buffer, and the resulting suspension or supernatant thereof can be used directly or after further dilution.
(2) Target Compound In the present invention, a labeled lectin is used as a labeling substance of a sandwich method. The labeled lectin recognizes and binds with a specific sugar chain. Accordingly, in the present invention, it is required that the target compound comprise a sugar chain.

Such a target compound is a compound which comprises a sugar chain and binds to a ligand (target compound-capturing substance of a sandwich method). Examples thereof include glycoproteins and glycolipids as well as their modified molecules and complexes, and preferred examples of the target compound include prostate-specific antigen (PSA) and other tumor markers (e.g., CA19-9, Forssman antigens, T antigens, Tn antigens and serial T antigens).
2. Immunoassay by Sandwich Method In the present invention, an immunoassay by a sandwich method is employed, and it may be a commonly used method and is not particularly restricted.
(1) Ligand (Target Compound-Capturing Substance of Sandwich Method)

The ligand (target compound-capturing substance of sandwich method) used in the present invention is a substance which specifically recognizes and binds to a target compound and does not interfere with the recognition of the sugar chain of the target compound by a labeled lectin used as a labeling substance in the sandwich method. The ligand is not particularly restricted as long as it is appropriate as a substance for capturing the target compound and, for example, an antibody, an aptamer or a synthetic peptide can be used. Particularly, a monoclonal antibody against the target compound is preferred. When a tumor antigen, a tumor marker or the like is the target compound, it is appropriate to use an antibody (e.g., monoclonal antibody) that specifically binds to the antigen as the ligand. For example, when a human PSA (prostate-specific antigen) is the target compound, an anti-human PSA antibody can be used.

The above-described ligand means a substance which specifically captures a target compound and encompasses not only complete antibodies but also arbitrary antibody fragments and derivatives, including complete antibodies as well as a variety of antibodies such as Fabs, Fab'$_2$s, CDRs, humanized antibodies, polyfunctional antibodies and single-chain antibodies (ScFvs).

In the present invention, as a ligand that is not an antibody, for example, if available, a receptor appropriate for the target compound can be used. The term "receptor" used herein refers to a protein that exists in/on cells, specifically recognizes a biologically active substance, and transmits and expresses its action. Examples thereof include intracellular receptors (i.e., nuclear receptors) which specifically bind to a steroid, thyroid hormone, vitamin A or D or the like capable of freely passing through plasma membrane; and cell surface receptors which specifically bind to a peptide hormone, growth factor, cytokine, catecholamine or the like incapable of freely passing through plasma membrane.

(2) Immobilization of Ligand

In a sandwich method, a ligand is usually used by being solid-phased (immobilized) on a support (solid phase). That is, a compound to be measured is captured on a support via an immobilized ligand.

Examples of the support on which a ligand is immobilized include insoluble polysaccharides such as agarose and cellulose; synthetic resins such as silicone resins, polystyrene resins, polyacrylamide resins, nylon resins and polycarbonate resins; and insoluble supports made of glass. These supports are used in the form of, for example, beads (mainly spherical) or a plate (mainly planar). As the beads, for example, magnetic beads or resin beads that are filled in a column or the like can be used. In the case of a plate-form support, for example, a multi-well plate (e.g., a 96 multi-well plate) or a biosensor chip can be used.

The ligand and the support can be bound with each other by a commonly used method such as chemical binding or physical adsorption. As the support, any commercially available one can be suitably used.

(a) Immobilization of Ligand Using Solid-Phase Layer

A ligand can also be immobilized on a support by arranging a solid-phase layer on the surface of the support on which the ligand is to be immobilized.

The solid-phase layer is a layer which has a three-dimensional structure for immobilization of a ligand on the surface of a support. This "three-dimensional structure" refers to the structure of the solid-phase layer in which immobilization of a ligand is not restricted to the two dimensions of the support surface (in the case of SPFS, the "sensor substrate" surface (and the vicinity thereof)) and can be expanded to the three-dimensional space free from the surface (see FIG. 3).

The solid-phase layer may be directly arranged on the support surface, or the below-described SAM is arranged on the support surface and the solid-phase layer may then be arranged thereon.

Such solid-phase layer preferably contains glucose, carboxymethylated glucose and a polymer constituted by at least one monomer selected from the group consisting of monomers included in any of vinyl esters, acrylic acid esters, methacrylic acid esters, olefins, styrenes, crotonic acid esters, itaconic acid diesters, maleic acid diesters, fumaric acid diesters, allyl compounds, vinyl ethers and vinyl ketones, and it is more preferred that the solid-phase layer contain a hydrophilic polymer, such as dextran or a derivative thereof, and a hydrophobic polymer constituted by a hydrophobic monomer(s) included in any of vinyl esters, acrylic acid esters, methacrylic acid esters, olefins, styrenes, crotonic acid esters, itaconic acid diesters, maleic acid diesters, fumaric acid diesters, allyl compounds, vinyl ethers and vinyl ketones. Dextran such as carboxymethyldextran (CMD) is particularly preferred from the standpoints of the biocompatibility, inhibition of non-specific adsorption reaction and high hydrophilicity.

The molecular weight of CMD is preferably 1 kDa to 5,000 kDa, more preferably 4 kDa to 1,000 kDa.

In cases where a measurement method using SPFS is employed, the solid-phase layer (composed of, for example, dextran or a derivative thereof) preferably has a density of less than 2 ng/mm$^2$. The density of the solid-phase layer can be adjusted as appropriate in accordance with the type of the polymer used therein. It is preferred that the polymer be immobilized on the below-described SAM in such a density range because assay signals are thereby stabilized and enhanced when a plasmon sensor is used in an assay method. It is noted here that the density of "Sensor Chip CM5" manufactured by Biacore Life Sciences was 2 ng/mm$^2$. This density was estimated to be 2 ng/mm$^2$ as a result of determining the average 2,000 RU for signals that were measured by an SPR-measuring instrument manufactured by Biacore Life Sciences using the CM5 substrate and a substrate having only a gold film.

In cases where a measurement method using SPFS is employed, the average thickness of the solid-phase layer is preferably 3 nm to 80 nm. The thickness of layer can be measured using an atomic force microscope (AFM) or the like. It is preferred that the average thickness of the solid-phase layer be in this range because assay signals are thereby stabilized and enhanced when a plasmon sensor is used in an assay method.

For a case where carboxymethyldextran (CMD) is used as a polymer contained in the solid-phase layer, a method of immobilizing carboxymethyldextran on the surface of SAM formed on the below-described metal thin film of SPFS will now be described concretely.

Carboxymethyldextran preferably has a molecular weight of 1 kDa to 5,000 kDa and, by immersing a substrate, on which a transparent support, a metal thin film and a SAM are laminated in the order mentioned, into MES-buffered physiological saline (MES) which contains 0.01 mg/mL to 100 mg/mL of the above-described carboxymethyldextran, 0.01 mM to 300 mM of N-hydroxysuccinimide (NHS) and 0.01 mM to 500 mM of water-soluble carbodiimide (WSC) for a period of 0.2 hours to 3.0 hours, carboxymethyldextran can be immobilized on the SAM.

The density of the resulting solid-phase layer can be adjusted by changing the number of reaction sites (the number of functional groups of the SAM), the ionic strength and pH of the reaction solution and the WSC concentration with respect to the number of carboxyl groups of the carboxymethyldextran molecule. Further, the average thickness of the solid-phase layer can be adjusted by changing the molecular weight of carboxymethyldextran and the reaction time.

As a method of immobilizing a ligand on the solid-phase layer, a known chemical bonding reaction, particularly a chemical bonding reaction used for antibody modification, can be applied. For example, a method in which a carboxyl group of a reactive functional group-containing polymer, such as carboxymethyldextran [CMD] of the solid-phase layer, is converted into an active ester using water-soluble carbodiimide [WSC] (e.g., 1-ethyl-3-(3-dimethylaminopropyl)carbodiimide hydrochloride [EDC]) and N-hydroxysuccinic acid imide [NHS] and the thus active-esterified carboxyl group and an amino group of a ligand are allowed to undergo dehydration reaction so as to immobilize the ligand, can be employed.

Further, when a ligand is directly immobilized on the below-described SAM, for example, a method of immobilizing the ligand by allowing the carboxyl group of the SAM to undergo dehydration reaction with the amino group of the ligand in the above-described manner can be employed.

(b) Immobilization of Ligand Using SAM (Self-Assembled Monolayer)

A ligand can also be immobilized on a support by arranging a SAM (Self-Assembled Monolayer) on the surface of the support on which the ligand is to be immobilized.

The SAM is formed as a scaffold for immobilization of a ligand, preferably a solid-phase layer, on the support surface on which the ligand is to be immobilized. When a measurement method using SPFS is employed, the SAM is formed on the metal thin film surface for the immobilization of the ligand (on the surface that is not in contact with the transparent support) for the purposes of not only providing a scaffold but also inhibiting metal quenching of molecular fluorescence in the use of a plasmon sensor in a sandwich assay.

As a monomolecule contained in the SAM, for example, a carboxyalkanethiol having about 4 to 20 carbon atoms (available from, for example, Dojindo Laboratories or Sigma-Aldrich Japan), particularly preferably 10-carboxy-1-decanethiol, is used. A carboxyalkanethiol having 4 to 20 carbon atoms is preferred because a SAM formed therefrom has small optical influence, that is, the SAM has properties of high transparency, low refractive index, small thickness and the like.

The method of forming such a SAM is not particularly restricted, and a conventionally known method can be employed.

A case where a measurement method using SPFS is employed will now be described as an example.

Specific examples of a method of forming a SAM on a metal thin film include a method of immersing a transparent support having a metal thin film formed thereon, on the surface of which metal thin film a layer composed of a mask material is further formed, into an ethanol solution containing 10-carboxy-1-decanethiol (manufactured by Dojindo Laboratories). In this manner, the thiol group of 10-carboxy-1-decanethiol is bound and immobilized with metal and self-assembled on the surface of the metal thin film to form a SAM.

Further, prior to the formation of SAM, a "spacer layer composed of a dielectric" may also be formed. In this case, the monomolecule contained in the SAM is not particularly restricted as long as it is a silane coupling agent which comprises an ethoxy group (or a methoxy group) that is hydrolyzed to yield a silanol group (Si—OH) and, on the other end, a reactive group such as an amino group, a glycidyl group or a carboxyl group, and a conventionally known silane coupling agent can be used.

The method of forming such a SAM is not particularly restricted, and a conventionally known method can be employed.

As a dielectric used for the formation of such a "spacer layer composed of a dielectric", a variety of optically transparent inorganic substances as well as natural or synthetic polymers can be used. Thereamong, silicon dioxide ($SiO_2$), titanium dioxide ($TiO_2$) or aluminum oxide ($Al_2O_3$) is preferably incorporated because of their chemical stability, production stability and optical transparency.

The thickness of the spacer layer composed of a dielectric is usually 10 nm to 1 mm and, from the standpoint of the resonance angle stability, it is preferably 30 nm or less, more preferably 10 to 20 nm. Meanwhile, from the standpoint of electric field enhancement, the thickness of the spacer layer is preferably 200 nm to 1 mm and, from the standpoint of the stability of the electric field-enhancing effect, it is more preferably 400 nm to 1,600 nm.

Examples of a method of forming the spacer layer composed of a dielectric include a sputtering method, an electron beam vapor deposition method, a thermal vapor deposition method, a method of forming a spacer layer by chemical reaction using a material such as polysilazane, and a coating method using a spin coater.

When a SAM is formed, a ligand can be immobilized by arranging a solid-phase layer on the SAM, or directly on the SAM.

(3) Labeled Lectin Used as Labeling Substance of Sandwich Method

In the present invention, a labeled lectin is used to label a target compound captured on the support (solid phase) via a ligand in the above-described 2.(2).

Lectins each bind to a specific sugar chain with high binding capacity in accordance with their types; however, they may also bind to other sugar chain(s) even though the binding capacity thereof is low. Therefore, in the present invention, as a labeled lectin, in order to improve the noise-reducing effect by an addition of the below-described sugar chain compound, it is preferred to use a lectin which binds to a sugar chain of a target compound with high binding capacity while binding to sugar chains of impurities contained in a biological sample, such as glycoproteins and glycolipids other than the target compound, with low binding capacity.

Examples of such lectin include:

(a) lectins belonging to various molecule families obtained from, for example, animals, plants, fungi, bacteria and viruses, that is, ricin B chain-related "R-type lectins" that are found throughout the biological world including bacteria;

(b) "calnexin and calreticulin" that generally exit in eukaryotes and are involved in folding of glycoproteins;

(c) calcium-requiring "C-type lectins" that widely exist in multicellular animals, including a large number of representative lectins such as "selectins" and "collectins";

(d) "galectins" that are widely distributed in the animal kingdom and shows specificity to galactose;

(e) "leguminous lectins" that form a large family in Leguminosae plants;

(f) "L-type lectins" that have structural similarity leguminous lectins and are involved in intracellular transport in animals;

(g) mannose 6-phosphate-binding "P-type lectins" that are involved in intracellular transport of lysosomal enzymes;

(h) "annexins" that bind to an acidic sugar chain such as glycosaminoglycan; and (i) "I-type lectins" that belong to an immunoglobulin superfamily, including "siglecs".

Specific examples of the above-described lectins include ACA (*Amaranthus caudatus* lectin), BPL (*Bauhinia purpurea* lectin), ConA (*Canavalia ensiformis* lectin), DBA (Horsegram lectin), DSA (*Datura stramonium* lectin), ECA (*Erythrina cristagalli* lectin), EEL (Spindle Tree lectin), GNA (*Galanthus nivalis* lectin), GSL I (*Griffonia simplicifolia* lectin), GSL II (*Griffonia simplicifolia* lectin), HHL (*Hippeastrum hybrid* lectin), jacalin (jackfruit lectin), LBA (Lima bean lectin), LCA (*Lens culinaris* lectin), LEL (*Lycopersicon esculentum* lectin), LTL (*Lotus tetragonolobus* lectin), MPA (*Maclura pomifera* lectin), NPA (*Narcissus pseudonarcissus* lectin), PHA-E (*Phaseolus Vulgaris* lectin), PHA-L (*Phaseolus Vulgaris* lectin), PNA (peanut lectin), PSA (*Pisum sativum* lectin), PTL-I (*Psophocarpus tetragonolobus* lectin), PTL-II (*Psophocarpus tetragonolobus* lectin), PWM (pokeweed lectin), RCA120 (*Ricinus communis* lectin), SBA (soybean lectin), SJA (*Sophora japonica* lectin), SNA (*Sambucus nigra* lectin), SSA (*Sambucus sieboldiana* lectin), STL (*Solanum tuberosum* lectin), TJA-I (*Trichosanthes japonica* lectin), TJA-II (*Trichosanthes japonica* lectin), UDA (common stinging nettle lectin), UEA I (*Ulex europaeus* lectin), VFA (*Vicia faba* lectin), VVA (*Vicia villosa* lectin), WFA (*Wisteria floribunda* lectin), WGA (wheat germ lectin), AAL (*Aleuria aurantia* lectin), and AOL (*Aspergillus oryzae* lectin).

A labeled lectin is obtained by conjugating (binding) any of these lectins with a label.

As the label, a label known to those of ordinary skill in the art, such as a fluorescent dye, an enzyme, a coenzyme, a chemiluminescent substance or a radioactive substance, can be used.

Examples of the fluorescent dye include organic fluorescent dyes such as fluorescent dyes of the fluorescein family (manufactured by Integrated DNA Technologies, Inc.), fluorescent dyes of the polyhalofluorescein family (manufactured by Applied Biosystems Japan, Ltd.), fluorescent dyes of the hexachlorofluorescein family (manufactured by Applied Biosystems Japan, Ltd.), fluorescent dyes of the coumarin family (manufactured by Invitrogen Corp.), fluorescent dyes of the rhodamine family (manufactured by GE Healthcare Bio-Sciences Corp.), fluorescent dyes of the cyanine family, fluorescent dyes of the indocarbocyanine family, fluorescent dyes of the oxazine family, fluorescent dyes of the thiazine family, fluorescent dyes of the squaraine family, fluorescent dyes of the chelated lanthanide family, fluorescent dyes of BODIPY (registered trademark) family (manufactured by Invitrogen Corp.), fluorescent dyes of the naphthalene sulfonate family, fluorescent dyes of the pyrene family, fluorescent dyes of the triphenylmethane family, and Alexa Fluor (registered trademark) dye series (manufactured by Invitrogen Corp.).

Further, examples of the fluorescent dye also include rare earth (e.g., Eu, Tb) complex-based fluorescent dyes such as ATBTA-Eu$^{3+}$; fluorescent proteins that are represented by blue fluorescent proteins (BFP), cyan fluorescent proteins (CFP), green fluorescent proteins (GFP), yellow fluorescent proteins (YFP), red fluorescent proteins (DsRed) and allophycocyanin (APC; LyoFlogen (registered trademark)); and particles of fluorescent such as latex, silica and the like.

When a sample derived from a blood specimen is analyzed, in order to minimize the effect of light absorption by iron originating from hemocytes in blood, it is desired to use a fluorescent dye having a maximum fluorescence wavelength in the near-infrared region, such as Cy5 or Alexa Fluor 647.

Examples of the radioactive substance include radio isotopes (such as $^{32}$P, $^{14}$C, $^{125}$I, $^{3}$H and $^{131}$I).

3. Sugar Chain Compound

It is generally considered that a lectin and a sugar chain are bound by an equilibrium reaction and that the binding strength is weaker than that of a bond between an antibody and an antigen. In addition, the specificity of a sugar chain in a bond between a lectin and the sugar chain is lower than that of an antigen in a bond between an antibody and the antigen. Therefore, in a sandwich method using a labeled lectin, by adding the labeled lectin and then adding other sugar chain compound, the sugar chain compound can be made to compete (cross) with impurities that are bound with the labeled lectin by an equilibrium reaction.

In the present invention, by an addition of a sugar chain compound, in binding between a labeled lectin and impurities such as glycoproteins and glycolipids, the sugar chain compound is allowed to compete (cross) with the impurities. Some of the impurities bound with the labeled lectin are thereby dissociated, and the dissociated labeled lectin and the added sugar chain compound are bound with each other. Consequently, the labeled lectin captured on a solid phase via impurities non-specifically bound to a ligand and the like is released. Further, by removing the labeled lectin released from the solid phase and bound with the sugar chain compound by washing or other method, the noise originating from the impurities in a sandwich method is reduced (see FIG. 2). In this case, the addition of the sugar chain compound potentially makes the sugar chain compound to also compete (cross) with the target compound bound with the labeled lectin and this may also cause the labeled lectin bound with the target compound to be dissociated, resulting in a reduction in the signal originating from the target compound. In order to inhibit this signal reduction as much as possible, it is preferred that the dissociation constant between the sugar chain compound and the labeled lectin that are added in the present invention be in a certain range.

Accordingly, the sugar chain compound to be added in the present invention is one which competes (crosses) with impurities in a biological sample for binding with a labeled lectin.

It is more preferred that, in the sugar chain compound to be added in the present invention, when the dissociation constant between the sugar chain compound to be added and the labeled lectin and the dissociation constant between the target compound and the labeled lectin are defined as "x" and "a", respectively, the x be in the range of x>a.

When the same sugar chain compound as the one contained in the solid-phase layer is added, the S/N ratio may not be sufficiently increased as compared to when no sugar chain compound is added. Thus, in such a case, it is preferred to add a sugar chain-containing compound that is different from the sugar chain compound (e.g., CMD) contained in the solid-phase layer.

(1) Sugar Chain Compound which Competes (Crosses) with Impurities in Biological Sample As described above, the sugar chain compound added in the present invention is one which competes (crosses) with impurities in a biological sample for binding with a labeled lectin. The term "compete (cross)" used in the present invention is synonymous with competition in general competitive inhibition and the like and refers to a relationship in which, when a lectin is used as a receptor, a substance and other substance compete to bind at the same binding site of the receptor in a reversible manner. In other words, the term "compete (cross)" encompasses not only competition for binding in which the binding site is precisely recognized at the molecular level, but also competition occurring between sugar chains that bind to the same binding region of a lectin.

As impurities that bind with a labeled lectin in a biological sample, glycoproteins and glycolipids are considered and, in the measurement of a biological sample by a sandwich method using a labeled lectin, a plurality of substances contained as impurities in the biological sample bind with the labeled lectin. Thus, in the present invention, any sugar chain compound can be used as long as it competes with at least some of the impurities binding to a labeled lectin in a biological sample, even when its competitive relationship with each impurity substance in the biological sample is unclear. However, the competition in binding with a labeled lectin can also occur between the added sugar chain compound and a target compound. Therefore, as the sugar chain compound to be added in the present invention, it is required to select one which exhibits greater the noise-reducing effect than the signal-reducing effect by examining the reduction in the noise originating from impurities and the reduction in the signal originating from the target compound in an actual measurement system of a sandwich method.

One example of a method of selecting a sugar chain compound to be added in the present invention is as follows (see Examples):

(i) in a measurement system of a sandwich method using a labeled lectin, a sugar chain compound is added to a biological sample and allowed to compete with impurities bound with the labeled lectin, and the signal intensity from which the signals of conjugates formed between the thus released labeled lectin and the added sugar chain compound are removed is measured (that is, the intensity of a sum of the post-competition "noise (N) originating from impurities" and "signal (s) originating from a target compound" (this sum is hereinafter simply referred to as "noise (N)") is measured); and (ii) after adding a reference standard of the target compound to the biological sample, a sugar chain compound is further added and the signal intensity is measured in the same manner as in the above (i) (that is, the intensity of a sum of the post-competition "signal (S) originating from the reference standard", "noise (N) originating from impurities" and "signal (s) originating from the target compound" (this sum is hereinafter simply referred to as "signal (S)") is measured). Then, a sugar chain compound which yields a large "S"/"N" ratio that conforms to the purpose of the measurement can be selected as the sugar chain compound to be added. For example, when the biological sample, the target compound and the labeled lectin of any of the below-described Examples are used, the sugar chain compound to be added has a S/N ratio of preferably not less than 3, more preferably not less than 4.

In this case, it is required that the addition of the reference standard of the target compound in the above (ii) be carried out within a range of the concentration of the target compound in an actual measurement. When an excessive amount of the reference standard is added, the intensity of the signal originating from the reference standard is increased, which leads to a large S/N ratio even when prominent competition occurs between the reference standard and the added sugar chain compound. Meanwhile, an excessively small amount of the reference standard leads to a small S/N ratio even when the sugar chain compound is effective in competing with impurities. Therefore, in order to properly understand the effect of the competition of the sugar chain compound in an actual measurement, it is required that the addition of the reference standard in the above (ii) be carried out within a range of the concentration of the target compound in an actual measurement.

As the biological sample used in the determination of the above-described S/N ratio, a biological sample which is used in an actual measurement or a biological sample which is considered to contain substantially the same impurities but contains no target compound (e.g., commercially available normal human pooled serum) may be employed.

(2) Sugar Chain Compound Having Dissociation Constant Within a Certain Range

As described above, in a preferred sugar chain compound to be added in the present invention, when the dissociation constant between the sugar chain compound to be added and the labeled lectin and the dissociation constant between the target compound and the labeled lectin are defined as "x" and "a", respectively, the x is in the range of x>a.

In the present invention, the dissociation constant is defined as follows.

The binding between a sugar chain compound (A) and a lectin (B) occurs through a reversible reaction, and the following formula is established in an equilibrium state (wherein, [A] represents the concentration of the sugar chain compound (mol/L); [B] represents the concentration of the lectin (mol/L); and [A–B] represents the concentration of conjugates formed between the sugar chain compound and the lectin (mol/L)).

$$[A-B] \leftrightarrows [A]+[B]$$

In this case, the dissociation constant, Kd, between the sugar chain compound (A) and the lectin (B) is represented by the following equation:

$$Kd=[A]\times[B]/[A-B]$$

As described above, the sugar chain compound to be added in the present invention is preferably one in which, in binding with a labeled lectin, the competition with a target compound is suppressed as much as possible while the competition with impurities is sufficiently generated, and it is also preferred that the x be in the above-described range of x>a.

(3) Examples of Sugar Chain Compound to be Added

Preferred examples of the sugar chain compound to be added in the present invention are as shown in Table 1 in accordance with the respective target compounds and the labeled lectins.

TABLE 1

| Target compound | Labeled lectin | Sugar chain compound to be added | Dissociation constant (Kd) | |
|---|---|---|---|---|
| | | | x | a |
| Prostate-specific antigen (PSA) | Trichosanthes japonica Lectin (TJA-II) | Galactosyl-ceramide (α-galactosyl-ceramide) | x = 7.2 × $10^{-4}$ | a = 1.0 × $10^{-6}$ |
| | | Fuc-2-Chol (see WO2008/081686) | x = 4.2 × $10^{-3}$ | |
| | | Galactosyl diglyceride | x = 1.8 × $10^{-4}$ | |
| | | 2'-fucosyl-D-lactose | x = 1.2 × $10^{-5}$ | |
| Prostate-specific antigen (PSA) | Wisteria floribunda lectin (WFA) | Fuc-2-Chol (see WO2008/081686) | x = 1.1 × $10^{-5}$ | a = 1.0 × $10^{-7}$ |
| α-feto-protein (AFP) | Lens culinaris lectin (LCA) | Man-2-Chol (see WO2008/081686) | x = 2.2 × $10^{-4}$ | a = 2.3 × $10^{-7}$ |
| α-feto-protein (AFP) | Sambucus sieboldiana lectin (SSA) | Fuc-2-Chol (see WO2008/081686) | x = 7.8 × $10^{-4}$ | a = 2.4 × $10^{-8}$ |

(4) Addition of Sugar Chain Compound

A sugar chain compound can be added after a labeled lectin is added and unreacted labeled lectin removed by washing, or simultaneously with the addition of a labeled lectin.

In cases where a sugar chain compound is added after the addition and washing of a labeled lectin, since the labeled lectin is already bound to the sugar chain of a target compound captured on a support (solid phase) via a ligand as well as the sugar chains of impurities non-specifically bound to the ligand and the like, it is believed that no free labeled lectin is present. In this case, the sugar chain compound can be added in such an amount that is required for attaining an effect of reducing the noise originating from the impurities.

In cases where a sugar chain compound is added simultaneously with the addition of a labeled lectin, since it is believed that unreacted labeled lectin is present, it is required to add the sugar chain compound in an amount that is sufficient for allowing the sugar chain compound to compete with impurities in binding with the labeled lectin. In other words, when the sugar chain compound is added in a small amount, the added sugar chain compound entirely reacts with unreacted labeled lectin, so that competition does not take place.

4. Measurement of Signal Intensity

In the measurement method of the present invention, the intensity of a signal generated by a labeled lectin captured on a support (solid phase) via a ligand and a target compound is measured.

The measurement method used in the present invention is not particularly restricted as long as it is capable of measuring the above-described signal generated by the labeled lectin, and the measurement can be performed in accordance with a method that is suitable for each labeling substance and known to those of ordinary skill in the art. For example, in cases where a lectin labeled with a radioactive substance is to be detected, the measurement can be performed by liquid scintillation or a RIA method. In cases where a lectin labeled with a fluorescent dye is to be detected, the measurement can be performed using a luminometer, SPFS measurement apparatus or the like. In cases where a lectin labeled with an enzyme is to be detected, the measurement can be performed by adding a substrate corresponding to the labeling enzyme and then measuring a chemical change of the substrate caused by the enzyme, such as color development, fluorescence or chemiluminescence.

As a measurement method to be used in the present invention, surface plasmon-field enhanced fluorescence spectroscopy (SPFS) is preferred. SPFS is a method which utilizes a phenomenon that, when an excitation light is irradiated to a metal thin film formed on a dielectric member at an angle that causes attenuated total reflection (ATR), an evanescent wave transmitting through the metal thin film is enhanced by several ten times to several hundred times due to resonance with surface plasmon, thereby efficiently exciting a fluorescent material labeling a target compound captured in the vicinity of the metal thin film so as to measure its fluorescent signal. Such SPFS is extremely sensitive as compared to common fluorescent labeling methods and the like; therefore, it is capable of quantifying a target compound even when it exists in a sample only in a trace amount. When SPFS is employed, the measuring member can take any constitution of a flow path or a well, and the sensor chip, the reaction layer, the SPFS system, the SPFS measurement apparatus and the like to be used can be those which are usually used.

5. Measurement of Target Compound in Biological Sample

In the measurement method of the present invention, a target compound contained in a biological sample can be quantified by sequentially carrying out the following steps (1) to (6):

(1) the step of introducing a biological sample to a measurement container (such as a well or a flow path) on which a ligand capable of binding with a target compound is immobilized and thereby allowing the target compound to bind with the ligand;

(2) the step of adding a labeled lectin to the measurement container resulting from the step (1) so as to allow the labeled lectin to bind with a sugar chain of the target compound;

(3) the step of removing unbound labeled lectin by washing the measurement container resulting from the step (2) with, for example, a phosphate buffer;

(4) the step of adding the sugar chain compound of the present invention to the measurement container resulting from the step (3) so as to allow sugar chains of impurities that are already bound with the labeled lectin to compete with the added sugar chain compound;

(5) the step of removing conjugates formed between the labeled lectin released from the support (solid phase) and the added sugar chain compound by washing the measurement container resulting from the step (4) with, for example, a phosphate buffer; and (6) the step of measuring a signal generated by the labeled lectin in the measurement container resulting from the step (5).

For quantification, for example, after adding a reference standard of the target compound to a commercially available biological sample (e.g., blood) and carrying out the above-described steps to prepare a calibration curve, the intensity of a signal obtained from the biological sample to be measured is applied to the calibration curve, thereby the concentration of the target compound in the biological sample can be determined.

It is noted here that the unbound labeled lectin and conjugates formed between the labeled lectin released from the solid phase and the sugar chain compound may also be removed simultaneously by performing the addition of the labeled lectin of the step (2) and the addition of the sugar chain compound of the step (4) at the same time with omission of the washing of the step (3) and then performing the washing of the step (5).

EXAMPLES

1. Measurement by Labeled Lectin Using SPFS (Comparative Examples: Without Addition of Competing Sugar Chain Compound)

(1-1) Fluorescent Labeling of TJA-II Lectin

TJA-II lectin [*Trichosanthes japonica* lectin] (manufactured by Seikagaku Corporation) was fluorescently labeled using Alexa Fluor (trademark) 647 Protein Labeling Kit (manufactured by Invitrogen Corp.). The procedures were carried out in accordance with the protocol attached to the kit. In order to remove unreacted lectin, unreacted fluorescent substance and the like, the reaction product was purified using an ultrafiltration membrane (manufactured by Nihon Millipore K.K.), and an Alexa Fluor 647-labeld TJA-II solution was thereby obtained. The thus obtained fluorescently labeled TJA-II lectin solution was subjected to protein quantification and then stored at 4° C.

(1-2) Preparation of LNCaP Culture Supernatant

LNCaP (human prostate adenocarcinoma cell line) producing PSA expressing a β-N-acetylgalactosamine residue was cultured, and the resulting supernatant was recovered and centrifuged. Then, the PSA concentration was measured by ELISA and the supernatant was stored at −80° C.

(1-3) Preparation of Sensor Chip

A 1 mm-thick glass-made transparent planar substrate "S-LAL 10" (manufactured by Ohara Inc., refractive index

[nd]=1.72) was plasma-cleaned using a plasma dry cleaner "PDC 200" (manufactured by Yamato Scientific Co., Ltd.). On one side of the thus plasma-cleaned substrate, a chromium thin film was first formed by a sputtering method and, on the surface thereof, a gold thin film was further formed by a sputtering method. The chromium thin film had a thickness of 1 to 3 nm and the gold thin film had a thickness of 44 to 52 nm.

Next, the thus obtained substrate was immersed for 24 hours in 10 mL of an ethanol solution of 10-carboxy-1-decanethiol adjusted to have a concentration of 25 mg/mL, thereby forming a SAM on the surface of the gold thin film. This support was taken out of the ethanol solution, washed sequentially with ethanol and isopropanol, and then dried using an air-blow gun. Subsequently, the support on which the SAM was thus formed was immersed for 1 hour in a pH7.4 MES-buffered physiological saline (MES) (ionic strength: 10 mM), which contained 1 mg/mL of carboxymethyldextran (CMD) having a molecular weight of 500,000, 0.5 mM of N-hydroxysuccinimide (NHS) and 1 mM of water-soluble carbodiimide (WSC), to immobilize CMD on the SAM. The substrate was further immersed in 1N aqueous NaOH solution for 30 minutes to hydrolyze unreacted succinic acid ester. On the surface of the resulting substrate, a flow path was formed by arranging a 0.5 mm-thick sheet-form silicone rubber spacer having a hole of 2 mm×14 mm in size, and a 2 mm-thick polymethyl methacrylate plate was placed and press-adhered thereon such that it covered the substrate from the outside of the flow path. The flow path and the polymethyl methacrylate were screw-fixed with each other.

Using a peristaltic pump, ultrapure water and then PBS were allowed to circulate in the flow path for 10 minutes and 20 minutes, respectively, at room temperature and a flow rate of 500 μL/min. Then, after feeding and circulating 5 mL of PBS containing 50 mM of N-hydroxysuccinimide (NHS) and 100 mM of water-soluble carbodiimide (WSC) for 20 minutes, 2.5 mL of an anti-PSA monoclonal antibody (Clone No. 79, 2.5 mg/mL; manufactured by Mikuri Immunolaboratory, Ltd.) solution (whose anti-PSA monoclonal antibody concentration was adjusted to be 20 μg/mL) was fed and circulated for 30 minutes to immobilize the primary antibody on the SAM. Lastly, a phosphate-buffered saline (PBS) containing 1% by weight of bovine serum albumin (BSA) was fed and circulated for 30 minutes to perform a nonspecific adsorption-inhibiting treatment, and two sensor chips were thereby prepared.

(1-4) Measurement

Antigen Addition Step: To one of the thus prepared sensor chip, 0.5 mL of a solution having a PSA concentration of 1.0 ng/mL, which was prepared by diluting the LNCaP culture supernatant with a commercially available serum (manufactured by Kohjin Bio Co., Ltd.), was added and circulated for 25 minutes in place of PBS. To the other sensor chip, a commercially available serum (manufactured by Kohjin Bio Co., Ltd.) containing no LNCaP culture supernatant was added and circulated for 25 minutes.

Washing Step: Each sensor chip was washed by circulating TBS containing 0.05% by weight of Tween 20 as a transfer liquid. Here, using a laser light source, the metal thin films of the sensor chip were irradiated with laser light having a wavelength of 635 nm, whose photon amount was adjusted by an optical filter (manufactured by Sigmakoki Co., Ltd.), through a prism ("S-LAL 10" manufactured by Ohara Inc. (refractive index [n]=1.72)), and the blank fluorescence was detected using a CCD image sensor (manufactured by Texas Instruments Inc.) equipped with a cut filter for cutting light having wavelengths of non-fluorescent components and an objective lens (×20).

Detection Step: First, 5 mL of PBS containing the fluorescently labeled lectin (1 ng/mL) prepared in the above (1-1) was added and circulated for 20 minutes. Then, 20 minutes after changing the transfer liquid to TBS solution containing 0.05% by weight of Tween 20, signals were obtained using a CCD image sensor (manufactured by Texas Instruments Inc.). As a result of this measurement, the signal (S) obtained from an experiment with an addition of the LNCaP culture supernatant was determined to have an intensity of 18,000 and the signal (N) obtained from an experiment without an addition of the LNCaP culture supernatant was determined to have an intensity of 8,900, so that the S/N ratio was calculated to be 2.

Further, also for each of the following cases, the same experiment as described above was carried out and the S/N ratio was determined:

(a) cases where a commercially available serum (manufactured by Kohjin Bio Co., Ltd.), a PSA, an anti-PSA monoclonal antibody, and *Wisteria floribunda* lectin (WFA; manufactured by Vector Laboratories, Inc.) were used as a biological sample, a target compound, a ligand and a labeled lectin, respectively; and (b) cases where α-fetoprotein (AFP; 2.0 mg/mL solution; manufactured by Acris Antibodies GmbH), an anti-AFP monoclonal antibody (Clone 1D5; 1.8 mg/mL; manufactured by Mikuri Immunolaboratory, Ltd.), and *Lens culinaris* lectin (LCA; manufactured by Vector Laboratories, Inc.), *Sambucus sieboldiana* lectin (SSA; manufactured by J-OIL Mills, Inc.) were used as a biological sample, target compound, ligand and labeled lectin, respectively.

In the above-described cases of (b), for immobilization of the primary antibody onto SAM in the above-described sensor chip preparation of (1-3), 2.5 mL of an anti-AFP monoclonal antibody solution (whose anti-AFP monoclonal antibody concentration was adjusted to be 50 μ/mL) was fed and circulated for 30 minutes. Also, in the above-described antigen addition step of (1-4), on one of the sensor chips, 0.5 mL of a solution having an AFP concentration of 3.0 ng/mL (which was prepared by diluting AFP with commercially available serum) was added and circulated for 25 minutes.

The results of these cases are shown in Table 2.

2. Measurement by Labeled Lectin Using SPFS (Examples: With Addition of Competing Sugar Chain Compound)

In the above-described detection step of 1, after adding PBS containing a fluorescently labeled lectin and washing each sensor chip with a TBS solution containing Tween 20, a PBS solution containing galactosylceramide (α-galactosylceramide, manufactured by Funakoshi Co., Ltd.), 2'-fucosyl-D-lactose (manufactured by Sigma-Aldrich Japan), galactosyl diglyceride (manufactured by Sigma-Aldrich Japan), Fuc-2-Chol (synthesized in accordance with the descriptions of WO2008/081686; see the structural formula shown below) or Man-2-Chol (synthesized in accordance with the descriptions of WO2008/081686; see the structural formula shown below) as a sugar chain compound at a concentration of 0.1% by weight was applied for 10 minutes, thereby allowing the added sugar chain compound to compete with impurities in the commercially available serum that were bound with a labeled lectin. Then, each sensor chip was washed by feeding thereto a TBS solution containing Tween 20 as a transfer liquid. Except these points, the same experiment as described above in 1. was carried out and the S/N ratio was calculated. The results thereof are shown in Table 2.

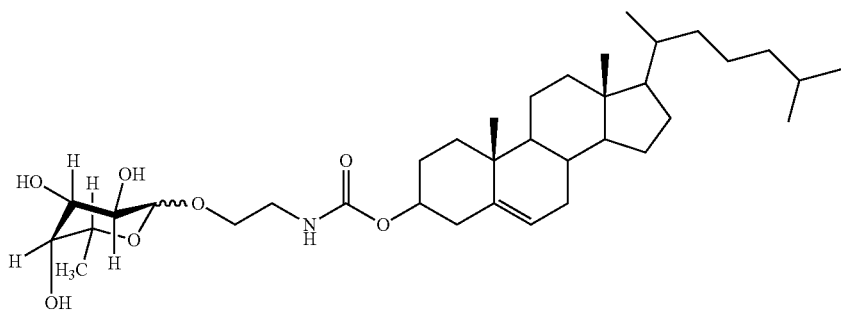

Fuc-2-chol
Molecular Weight: 619.87

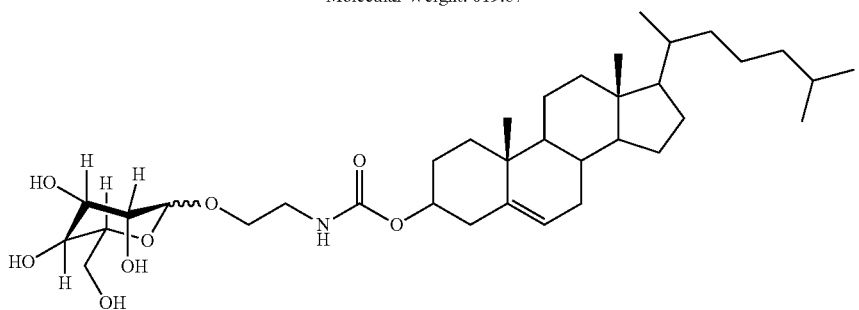

Man-2-chol
Molecular Weight: 635.87

(Note) In the above-described structural formulae, the wavy lines represent that the steric structure at the anomeric position of each sugar is an α-isomer and/or a β-isomer. The synthesized sugar chain compounds described above are each a mixture of α and β-isomers and have a sugar structure composed of a mixture of D and L-isomers.

TABLE 2

| Target compound | Labeled lectin | Added sugar chain compound | S/N | Note |
|---|---|---|---|---|
| Prostate-specific antigen (PSA) | *Trichosanthes japonica* Lectin (TJA-II) | Galactosyl-ceramide | 3 | Example (x > a) |
| | | 2'-fucosyl-D-lactose | 3 | Example (x > a) |
| | | Galactosyl diglyceride | 4 | Example (x > a) |
| | | Fuc-2-Chol (see WO2008/081686) | 4 | Example (x > a) |
| | | none | 2 | Comparative Example |
| Prostate-specific antigen (PSA) | *Wisteria floribunda* lectin (WFA) | Fuc-2-Chol (see WO2008/081686) | 3 | Example (x > a) |
| | | none | 2 | Comparative Example |
| α-feto-protein (AFP) | *Lens culinaris* lectin (LCA) | Man-2-Chol (see WO2008/081686) | 3 | Example (x > a) |
| | | none | 2 | Comparative Example |
| α-feto-protein (AFP) | *Sambucus sieboldiana* lectin (SSA) | Fuc-2-Chol (see WO2008/081686) | 3 | Example (x > a) |
| | | none | 1 | Comparative Example |

DESCRIPTION OF SYMBOLS

1: Ligand (target compound-capturing substance)
2: Target compound comprising sugar chain
3: Impurity comprising sugar chain in biological sample
4: Sugar chain recognized by labeled lectin
5: Sugar chain not recognized by labeled lectin
6: Solid-phase layer (e.g., CMD for immobilization of a ligand on a support)
7: Support (e.g., a microplate well or a transparent support/metal thin film for SPFS)
7a: Metal thin film
7b: Transparent support (prism)
8: Labeled lectin
9: Sugar chain compound added in the present invention
10: Solid-phase layer (carboxymethyldextran (CMD))
11: SAM

The invention claimed is:

1. A method of measuring the amount of a target compound comprising a sugar chain in a biological sample by a sandwich immunoassay method using a ligand selected from the group consisting of antibody, aptamer, synthetic peptide and receptor, and a labeled lectin, said method comprising
releasing a labeled lectin which is bound with impurities on a solid-phase by adding a sugar chain compound to allow said labeled lectin to bind to said sugar chain compound, and
removing said labeled lectin bound with said sugar chain compound to reduce the noise originating from the impurities bound with said labeled lectin,
wherein, when the dissociation constant between said sugar chain compound to be added and said labeled lectin and the dissociation constant between said target compound and said labeled lectin are defined as "x" and "a", respectively, said x is in a range of x>a.

2. The method according to claim 1, wherein said target compound comprising a sugar chain in said biological sample to be measured is a tumor marker.

3. The method according to claim 2, wherein the combination of said target compound, said labeled lectin and said sugar chain compound to be added is any of the following combinations of (1) to (4):
(1) said target compound is a prostate-specific antigen (PSA), said labeled lectin is *Trichosanthes japonica* lectin (TJA-II), and said sugar chain compound to be added is a sugar chain compound containing fucose residue or a sugar chain compound containing galactose residue;
(2) said target compound is a prostate-specific antigen (PSA), said labeled lectin is *Wisteria floribunda* lectin (WFA), and said sugar chain compound to be added is a sugar chain compound containing fucose residue;
(3) said target compound is alpha-fetoprotein (AFP), said labeled lectin is *Lens culinaris* lectin (LCA), and said sugar chain compound to be added is a sugar chain compound containing mannose residue; and
(4) said target compound is alpha-fetoprotein (AFP), said labeled lectin is *Sambucus sieboldiana* lectin (SSA), and said sugar chain compound to be added is a sugar chain compound containing fucose residue.

4. The method according to claim 3, wherein a solid-phase layer used for immobilizing said ligand on a support comprises a sugar chain compound, said method comprising adding a sugar chain compound different from said sugar chain compound.

5. The method according to claim 3, comprising measuring florescence emitted by said labeled lectin by surface plasmon-field enhanced fluorescence spectroscopy (SPFS).

6. The method according to claim 4, comprising measuring florescence emitted by said labeled lectin by surface plasmon-field enhanced fluorescence spectroscopy (SPFS).

7. The method according to claim 1, wherein the combination of said target compound, said labeled lectin and said sugar chain compound to be added is any of the following combinations of (1) to (2): 1) said target compound is a prostate-specific antigen (PSA), said labeled lectin is *Trichosanthes japonica* lectin (TJA-II), and said sugar chain compound to be added is a sugar chain compound containing fucose residue or a sugar chain compound containing galactose residue; and (2) said target compound is a prostate-specific antigen (PSA), said labeled lectin is *Wisteria floribunda* lectin (WFA), and said sugar chain compound to be added is a sugar chain compound containing fucose residue.

8. The method according to claim 7, wherein a solid-phase layer used for immobilizing said ligand on a support comprises a sugar chain compound, said method comprising adding a sugar chain compound different from said sugar chain compound.

9. The method according to claim 7, comprising measuring florescence emitted by said labeled lectin by surface plasmon-field enhanced fluorescence spectroscopy (SPFS).

10. The method according to claim 8, comprising measuring florescence emitted by said labeled lectin by surface plasmon-field enhanced fluorescence spectroscopy (SPFS).

11. The method according to claim 1, wherein a solid-phase layer used for immobilizing said ligand on a support comprises a sugar chain compound, said method comprising adding a sugar chain compound different from said sugar chain compound.

12. The method according to claim 11, comprising measuring florescence emitted by said labeled lectin by surface plasmon-field enhanced fluorescence spectroscopy (SPFS).

13. The method according to claim 1, comprising measuring florescence emitted by said labeled lectin by surface plasmon-field enhanced fluorescence spectroscopy (SPFS).

14. The method according to claim 1, wherein the combination of said target compound, said labeled lectin and said sugar chain compound to be added is any of the following combinations of (1) to (2): (1) said target compound is alpha-fetoprotein (AFP), said labeled lectin is *Lens culinaris* lectin (LCA), and said sugar chain compound to be added is a sugar chain compound containing mannose residue; and (2) said target compound is alpha-fetoprotein (AFP), said labeled lectin is *Sambucus sieboldiana* lectin (SSA), and said sugar chain compound to be added is a sugar chain compound containing fucose residue.

15. The method according to claim 14, wherein a solid-phase layer used for immobilizing said ligand on a support comprises a sugar chain compound, said method comprising adding a sugar chain compound different from said sugar chain compound.

16. The method according to claim 14, comprising measuring florescence emitted by said labeled lectin by surface plasmon-field enhanced fluorescence spectroscopy (SPFS).

17. The method according to claim 15, comprising measuring florescence emitted by said labeled lectin by surface plasmon-field enhanced fluorescence spectroscopy (SPFS).

* * * * *